(12) United States Patent
Ito (10) Patent No.: US 6,743,177 B2
(45) Date of Patent: Jun. 1, 2004

(54) PUNCTURING NEEDLE GUIDE, ULTRASONIC PROBE, AND ULTRASOUND IMAGING APPARATUS

(75) Inventor: Hiroki Ito, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/408,475

(22) Filed: Apr. 7, 2003

(65) Prior Publication Data

US 2003/0195425 A1 Oct. 16, 2003

(30) Foreign Application Priority Data

Apr. 10, 2002 (JP) ........................ 2002-107300

(51) Int. Cl.⁷ ................................................ A61B 8/14
(52) U.S. Cl. ....................................................... 600/461
(58) Field of Search ................................ 600/437, 461; 606/130, 96; 128/916

(56) References Cited

U.S. PATENT DOCUMENTS

| | | |
|---|---|---|
| 4,058,114 A | 11/1977 | Soldner |
| 4,349,027 A | 9/1982 | DiFrancesco |
| 4,469,106 A * | 9/1984 | Harui ........................ 600/461 |
| 4,838,506 A | 6/1989 | Cooper |
| 4,899,756 A | 2/1990 | Sonek |
| 5,235,987 A | 8/1993 | Wolfe |
| 5,427,108 A | 6/1995 | Bollinger |
| 5,494,039 A | 2/1996 | Onik et al. |
| 5,623,931 A * | 4/1997 | Wung et al. ................ 600/461 |
| 5,647,373 A | 7/1997 | Paltieli |
| 5,758,650 A * | 6/1998 | Miller et al. ................ 600/461 |
| 5,941,889 A * | 8/1999 | Cermak ....................... 606/130 |
| 6,203,499 B1 | 3/2001 | Imling et al. |
| 6,361,499 B1 * | 3/2002 | Bates et al. ................. 600/461 |
| 6,368,280 B1 | 4/2002 | Cermak et al. |
| 6,379,307 B1 | 4/2002 | Filly et al. |
| 6,475,152 B1 | 11/2002 | Kelly, Jr. et al. |

* cited by examiner

Primary Examiner—Dennis W. Ruhl
Assistant Examiner—Ruby Jain
(74) Attorney, Agent, or Firm—Carl B. Horton, Esq.; Armstrong Teasdale LLP (57) ABSTRACT

A puncturing needle guide includes a plate-like body whose width diminishes gradually from one end thereof to the other end thereof; a plurality of holes which are formed in an end surface of the puncturing needle guide at one end thereof and through which a puncturing needle can be passed; a single hole which is formed in an end surface of the puncturing needle guide at the other end thereof and through which the puncturing needle can be passed; a hollow that is formed inside the plate-like body and that allows the plurality of holes and the single hole to communicate with one another; and an attachment which is formed along an edge of the plate-like body in a width direction thereof and by which the plate-like body is attached to an ultrasonic probe.

16 Claims, 6 Drawing Sheets

PUNCTURING NEEDLE GUIDE, ULTRASONIC PROBE, AND ULTRASOUND IMAGING APPARATUS

CROSS REFERENCE TO RELATED APPLICATIONS

This application claims the benefit of Japanese Application No. 2002-107300 field Apr. 10, 2002.

BACKGROUND OF THE INVENTION

The present invention relates to a puncturing needle guide, an ultrasonic probe, and an ultrasound imaging system. More particularly, the present invention is concerned with a puncturing needle guide required for performing biopsy using a puncturing needle, an ultrasonic probe including the puncturing needle guide, and an ultrasound imaging system including the ultrasonic probe.

When biopsy is performed on a patient's intracorporeal tissue, a puncturing needle is penetrated at the sight of a real-time tomographic image of a lesion. The real-time tomographic image is produced through ultrasound imaging or the like. An ultrasound imaging system includes an ultrasonic probe that transmits ultrasonic waves to an object and receives echoes of the ultrasonic waves, and an image production unit that produces an image on the basis of the echoes.

For penetrating the puncturing needle, a puncturing needle guide is attached to the ultrasonic probe. The puncturing needle guide has a through hole, that is, a guide hole through which the puncturing needle is passed. The direction of penetration is determined with the direction of a center axis of the guide hole.

A transvaginal probe is one type of ultrasonic probe. The transvaginal probe is generally a rod-like probe having an ultrasound transmitting/receiving member incorporated in the distal part thereof. The puncturing needle guide to be attached to the probe for use has one guide hole.

For transvaginal imaging or penetration, since the puncturing needle guide has only one guide hole, penetration is possible in only one direction. Therefore, if a target direction disagrees with the penetration-enabled direction, penetration is impossible to do.

SUMMARY OF THE INVENTION

Therefore, an object of the present invention is to realize a puncturing needle guide that enables penetration in a plurality of directions, an ultrasonic probe having the puncturing needle guide, and an ultrasound imaging system having the ultrasonic probe.

(1) According to one aspect of the present invention that attempts to solve the aforesaid problem, there is provided a puncturing needle guide having: a plate-like body whose width diminishes gradually from one end thereof to the other end thereof; a plurality of holes which are formed in an end surface of the plate-like body at one end thereof and through which a puncturing needle can be passed; a single hole which is formed in an end surface of the plate-like body at the other end thereof and through the puncturing needle can be passed; a hollow that is formed as an internal space of the plate-like body and that allows the plurality of holes and the single hole to communicate with one another; and an attachment that is formed along an edge of the plate-like body in a width direction thereof, and that enables attachment of the plate-like body to an ultrasonic probe.

According to the aspect of the present invention set forth in (1), a puncturing needle guide includes: a plate-like body whose width diminishes gradually from one end thereof to the other end thereof; a plurality of holes which are formed in an end surface of the plate-like body at one end thereof and through which a puncturing needle can be passed; a single hole which is formed in an end surface of the plate-like body at the other end thereof and through which the puncturing needle can be passed; a hollow that is formed as an internal space of the plate-like body and that allows the plurality of holes and the single hole to communicate with one another; an attachment that is formed along an edge of the plate-like body in a width direction thereof and that enables attachment of the plate-like body to an ultrasonic probe. Thus, a puncturing needle guide enabling penetration of the puncturing needle in a plurality of directions is realized.

Preferably, the attachment enables attachment of the plate-like body to a rod-like ultrasonic probe having an ultrasound transmitting/receiving member incorporated in the distal part thereof so that the other end of the plate-like body and the ultrasound transmitting/receiving member of the ultrasonic probe will be located on the same side of the ultrasonic probe. In this case, the puncturing needle guide can be inserted into a body cavity together with the ultrasonic probe.

(2) According to another aspect of the present invention that attempts to solve the aforesaid problem, there is provided an ultrasonic probe including: a rod-like body having an ultrasound transmitting/receiving member incorporated in the distal part thereof; a plate-like body whose width diminishes gradually from one end thereof to the other end thereof; a coupler that is formed alone an edge of the plate-like body in a width direction thereof and that couples the plate-like body to the rod-like body so that the other end of the plate-like body and the ultrasound transmitting/receiving member of the rod-like body will be located on the same side of the ultrasonic probe; a plurality of holes which are formed in an end surface of the plate-like body at one end thereof and through which a puncturing needle can be passed; a single hole which is formed in an end surface of the plate-like member at the other end thereof and through which the puncturing needle can be passed; and a hollow that is formed as an internal space of the plate-like body and that allows the plurality of holes and the single hole to communicate with one another.

According to the aspect of the present invention set forth in (2), an ultrasonic probe includes: a rod-like body having an ultrasound transmitting/receiving member incorporated in the distal part thereof; a plate-like body whose width diminishes gradually from one end thereof to the other end thereof; a coupler that is formed along en edge of the plate-like body in a width direction thereof and that couples the plate-like body to the rod-like body so that the other end of the plate-like body and the ultrasound transmitting/receiving member of the rod-like body will be located on the same side of the ultrasonic probe; a plurality of holes which are formed in an end surface of the plate-like body at one end thereof and through which a puncturing needle can be passed; a single hole which is formed in an end surface of the plate-like body at the other end thereof and through which the puncturing needle can be passed; and a hollow that is formed as an internal space of the plate-like body and that allows the plurality of holes and the single hole to communicate with one another. Thus, an ultrasonic probe having a puncturing needle guide that enables penetration of a puncturing needle in a plurality of directions is realized.

(3) According to still another aspect of the present invention that attempts to solve the aforesaid problem, there is provided an ultrasound imaging system comprising an ultrasonic probe that transmits ultrasonic waves to an object and receives echoes of the ultrasonic waves, and an image producing means for producing an image on the basis of the received echoes. The ultrasonic probe includes: a rod-like body having an ultrasound transmitting/receiving member incorporated in the distal part thereof; a plate-like body whose width diminishes gradually from one end thereof to the other end thereof; a coupler that is formed along an edge of the plate-like body in a width direction thereof and that couples the plate-like body to the rod-like body so that the other end of the plate-like body and the ultrasound transmitting/receiving member of the rod-like body will be located on the same side of the ultrasonic probe; a plurality of holes which are formed in an end surface of the plate-like body at one end thereof and through which a puncturing needle can be passed; a single hole which is formed in an end surface of the plate-like member at the other end thereof and through which the puncturing needle can be passed; and a hollow that is formed as an internal space of the plate-like body and that allows the plurality of holes and the single hole to communicate with one another.

According to the aspect of the present invention set forth in (3), an ultrasound imaging system comprises an ultrasonic probe that transmits ultrasonic waves to an object and receives echoes of the ultrasonic waves, and an image producing means for producing an image on the basis of the received echoes. The ultrasonic probe includes: a rod-like body having an ultrasound transmitting/receiving member incorporated in the distal part thereof; a plate-like body whose width diminishes gradually from one end thereof to the other end thereof; a coupler that is formed along an edge of the plate-like body in a width direction thereof and that couples the plate-like body to the rod-like body so that the other end of the plate-like body and the ultrasound transmitting/receiving member of the rod-like body will be located on the same side of the ultrasonic probe; a plurality of holes which are formed in an end surface of the plate-like body at one end thereof and through which a puncturing needle can be passed; a single hole which is formed in an end surface of the plate-like member at the other end thereof and through which the puncturing needle can be passed; and a hollow that is formed as an internal space of the plate-like body and that allows the plurality of holes and the single hole to communicate with one another. Thus, an ultrasound imaging system including an ultrasonic probe that has a puncturing needle guide which enables penetration of a puncturing needle in a plurality of directions is realized.

Preferably, the plurality of holes is formed in a row in the end surface. This helps grasp a direction of penetration.

Preferably, the internal surfaces of the plurality of holes are metallic surfaces. In this case, the internal surfaces will not be damaged with the puncturing needle.

Preferably, the internal surface of the single hole is a metallic surface. In this case, the internal surface will not be damaged with the puncturing needle.

Preferably, the internal surface of the hollow is a metallic surface. In this case, the internal surface will not be damaged with the puncturing needle.

Therefore, the present invention makes it possible to realize a puncturing needle guide that enables penetration in a plurality of directions, an ultrasonic probe including the puncturing needle guide, and an ultrasound imaging system including the ultrasonic probe.

Further objects and advantages of the present invention will be apparent from the following description of the preferred embodiments of the invention as illustrated in the accompanying drawings.

DETAILED DESCRIPTION OF THE INVENTION

Figure 1:
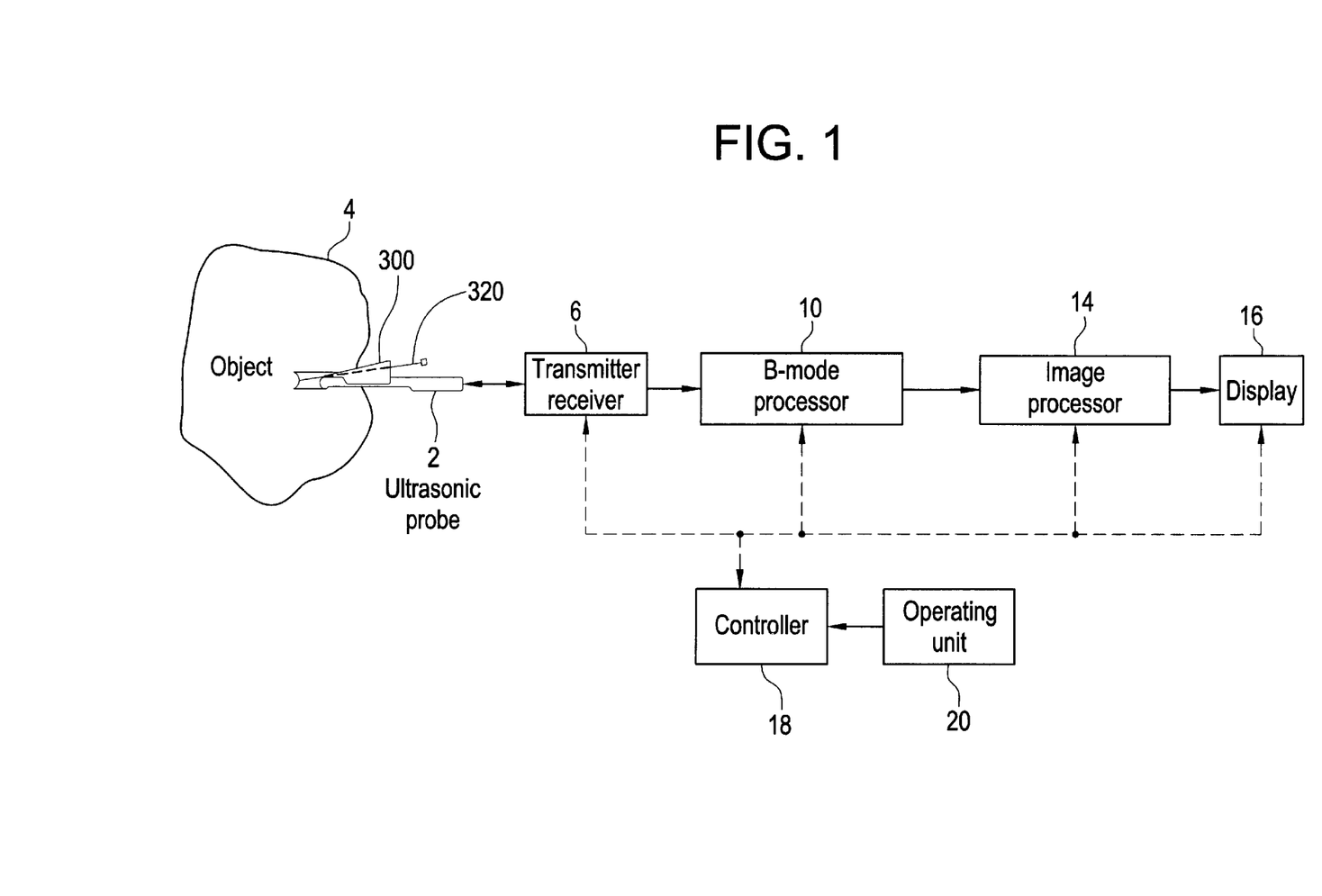
FIG. 1 is a block diagram showing a system of an example of an embodiment of the present invention.

Referring to the drawings, embodiments of the present invention will be described below. FIG. 1 is a block diagram of an ultrasound imaging system. The ultrasound imaging system is an example of an embodiment of the present invention. The system configuration presents an example of the embodiment of an ultrasound imaging system in accordance with the present invention.

As shown in FIG. 1, the ultrasound imaging system includes an ultrasonic probe 2. The ultrasonic probe 2 is an example of an embodiment of an ultrasonic probe in accordance with the present invention. The ultrasonic probe 2 will be described later. Generally speaking, the ultrasonic probe 2 includes an array of a plurality of ultrasonic transducers not shown. The respective ultrasonic transducers are made of a piezoelectric material, for example, PZT that is one form of a titanate zirconate lead ceramic.

An operator inserts the ultrasonic probe 2 into a body cavity of an object 4, for example, the vagina or rectum. The ultrasonic probe 2 has a puncturing needle guide 300. The puncturing needle guide 300 is used to penetrate a puncturing needle 320. The puncturing needle guide 300 is an example of an embodiment of a puncturing needle guide in accordance with the present invention. The puncturing needle guide 300 will be described later.

The ultrasonic probe 2 is connected to a transmitter receiver 6. The transmitter receiver 6 applies a driving signal to the ultrasonic probe 2 and thus causes the ultrasonic probe 2 to transmit ultrasonic waves. The transmitter receiver 6 receives echoes returned to the ultrasonic probe 2.

Figure 2:
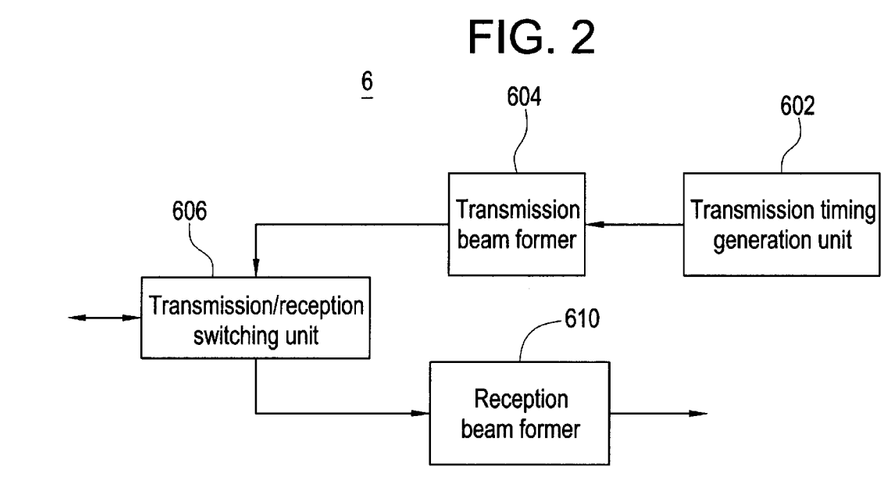
FIG. 2 is a block diagram showing a transmitter receiver included in the system of the example of the embodiment of the present invention.

FIG. 2 is a block diagram of the transmitter receiver 6. As illustrated, the transmitter receiver 6 includes a transmission timing generation unit 602. The transmission timing generation unit 602 periodically generates a transmission timing signal and transfers it to a transmission beam former 604. The cycle of the transmission timing signal is controlled by a controller 18 that will be described later.

The transmission beam former 604 forms a beam to be transmitted, that is, produces a beam-forming signal for use in forming an ultrasonic beam oriented in a predetermined direction according to a transmission timing signal. The beam-forming signal includes a plurality of driving signals each being given a time lag associated with a direction. The controller 18 that will be described later controls beam forming. The transmission beam former 604 transfers the transmission beam-forming signal to a transmission/reception switching unit 606.

The transmission/reception switching unit 606 transfers the beam-forming signal to the ultrasonic transducer array. In the ultrasonic transducer array, the plurality of ultrasonic transducers forming a transmission aperture generates ultrasonic waves each of which is given a phase difference proportional to a time lag exhibited by one driving signal. The wavefronts of the ultrasonic waves are synthesized with one another, whereby an ultrasonic beam is formed along a sound ray oriented in a predetermined direction.

A reception beam former 610 is connected to the transmission/reception switching unit 606. The transmission/reception switching unit 606 transfers a plurality of echoes received by the reception aperture formed within the ultrasonic transducer array to the reception beam former 610. The reception beam former 610 forms a beam to be received in consideration of the sound ray along which transmission has been performed. Specifically, the reception beam former 610 gives a time lag to the plurality of echoes so as to adjust the phases of the echoes, and then adds up the echoes so as to produce an echo reception signal that travels along a sound ray oriented in a predetermined direction. The controller 18 that will be described later controls the reception beam forming.

Transmission of an ultrasonic beam is repeated at intervals of a predetermined time according to the transmission timing signal generated by the transmission timing generation unit 602. Accordingly, the transmission beam former 604 and reception beam former 610 change directions of sound rays in units of a predetermined magnitude. Consequently, the interior of the object 4 is scanned with the ultrasonic beam propagated in a direction determined with a sound ray.

Figure 3:
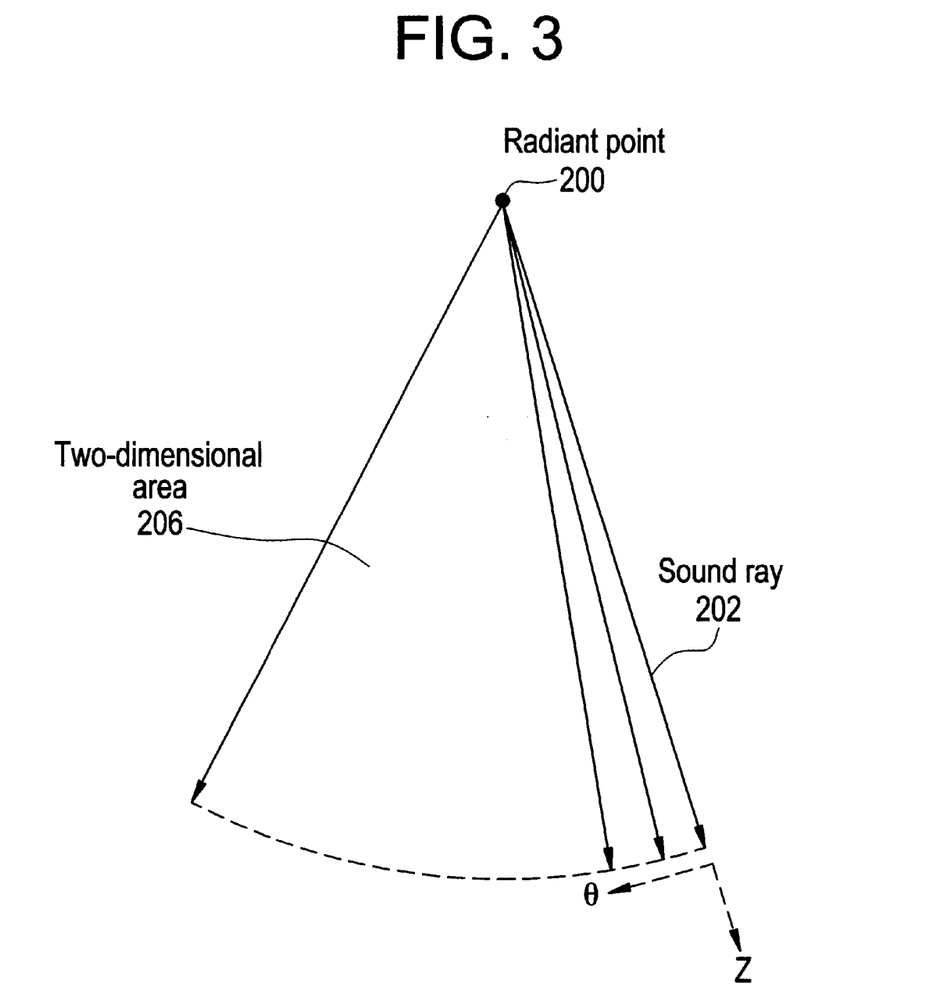
FIG. 3 is an illustrative diagram showing sound rays along which the system of the example of the embodiment of the present invention scans an object.

The transmitter receiver 6 having the foregoing components scans the interior of the object as, for example, shown in FIG. 3. Specifically, the transmitter receiver 6 scans a fan-shaped two-dimensional area 206 along a sound ray 202, which travels in a z direction from a radiant point 200, in a θ direction, and thus performs so-called sector scanning. When the transmitter receiver 6 scans an object along a sound ray, the scanning is not limited to the sector scanning but may be, for example, convex scanning.

The transmitter receiver 6 is connected to a B-mode processor 10. An echo reception signal produced to travel along a sound ray and sent from the transmitter receiver 6 is transferred to the B-mode processor 10. The B-mode processor 10 produces B-mode image data.

Figure 4:
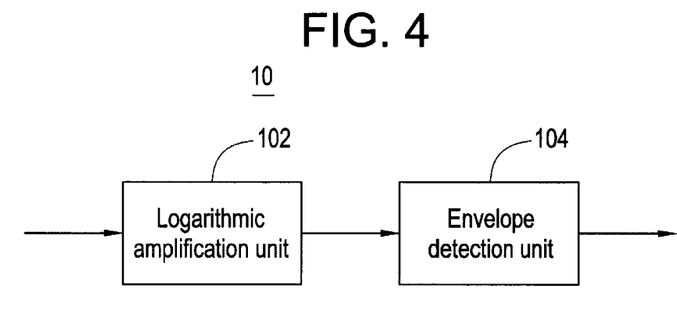
FIG. 4 is a block diagram showing a B-mode processor included in the system of the example of the embodiment of the present invention.

The B-mode processor 10 includes, as shown in FIG. 4, a logarithmic amplification unit 102 and an envelope detection unit 104. The B-mode processor 10 uses the logarithmic amplification unit 102 to logarithmically amplify an echo reception signal. The envelope detection unit 104 detects the envelope of the echo reception signal, and produces an A-scope signal that is a signal representing the intensity of an echo returning from each reflecting point on a sound ray. An instantaneous amplitude of the A-scope signal is regarded a luminance value, whereby B-mode image data is produced.

The B-mode processor 10 is connected to an image processor 14. The image processor 14 produces a B-mode image according to data received from the B-mode processor 10.

Figure 5:
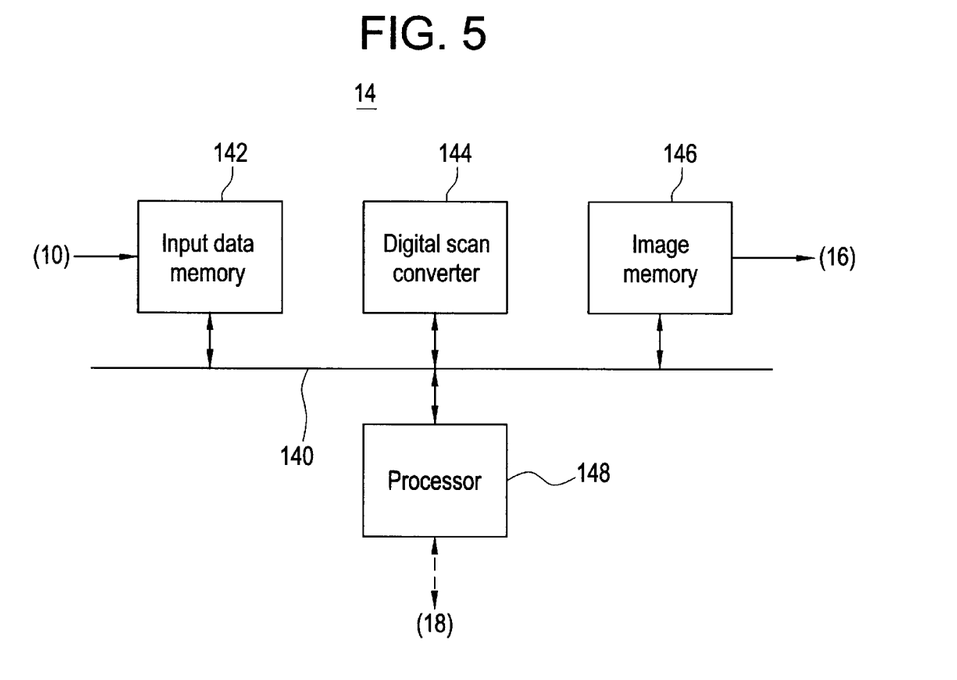
FIG. 5 is a block diagram showing an image processor included in the system of the example of the embodiment of the present invention.

The image processor 14 includes, as shown in FIG. 5, an input data memory 142, a digital scan converter 144, an image memory 146, and a processor 148 which are interconnected via a bus 140.

B-mode image data and Doppler image data received in relation to each sound ray from the B-mode processor 10 are stored in the input data memory 142. The data in the input data memory 142 is scanned and converted by the digital scan converter 144 and stored in the image memory 146. The processor 148 performs predetermined data processing on the data in the input data memory 142 and the one in the image memory 146.

A display 16 is connected to the image processor 14. The display 16 receives an image signal from the image processor 14 and displays an image according to the image signal. The display 16 is realized with a graphic display or the like capable of displaying a color image. The transmitter receiver 6, B-mode processor 10, image processor 14, and display 16 constitute an example of an image producing means included in the present invention.

The controller 18 is connected to the transmitter receiver 6, B-mode processor 10, image processor 14, and display 16. The controller 18 gives a control signal to each of the components so-as to control the actions thereof. The controller 18 receives various report signals from the respective controlled components. B-mode imaging is performed under the control of the controller 18.

An operating unit 20 is connected to the controller 18. The operating unit 20 is manipulated by an operator and used to enter an appropriate command or information that will be transmitted to the controller 18. The operating unit 20 is realized with an operator panel including, for example, a keyboard, a pointing device, and other operating instruments.

Figure 6:
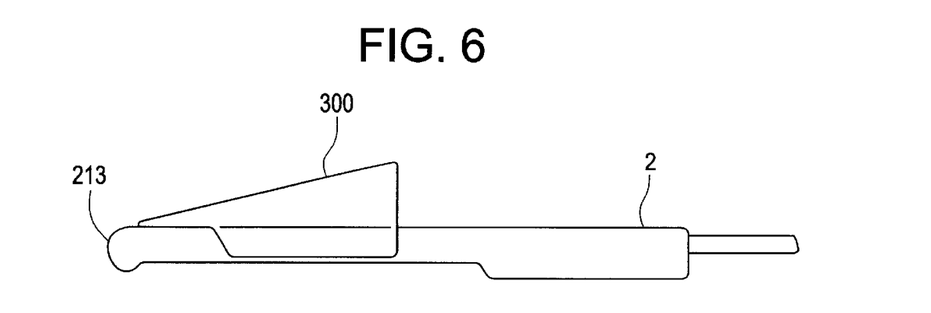
FIG. 6 shows the appearance of an ultrasonic probe.

FIG. 6 schematically shows the appearance of the ultrasonic probe 2. As illustrated, the ultrasonic probe 2 is shaped substantially like a rod. The overall length of the rod-like body is, for example, 300 mm. The section of the rod-like body is substantially round. The left side of the ultrasonic probe 2 in FIG. 6 is a portion to be inserted into a body cavity. The ultrasonic probe 2 is inserted into a body cavity by a length of up to 60 mm.

The ultrasonic probe has an ultrasound transmitting/receiving member 213 incorporated in the distal part thereof that is inserted into a body cavity. The ultrasound transmitting/receiving member. 213 is constituted of the ultrasonic transducer array. The right side of the ultrasonic probe 2 in FIG. 6 serves as a hand-held portion. An operator holds the hand-held portion so as to manipulate the ultrasonic probe 2.

The ultrasonic probe 2 includes a puncturing needle guide 300. The puncturing needle guide 300 is attached to the portion of the ultrasonic probe 2 that is inserted into a body cavity. The puncturing needle guide 300 is manufactured separately and attached to the ultrasonic probe 2. Incidentally, the puncturing needle guide 300 may be integrated with the ultrasonic probe 2.

Figure 7A:
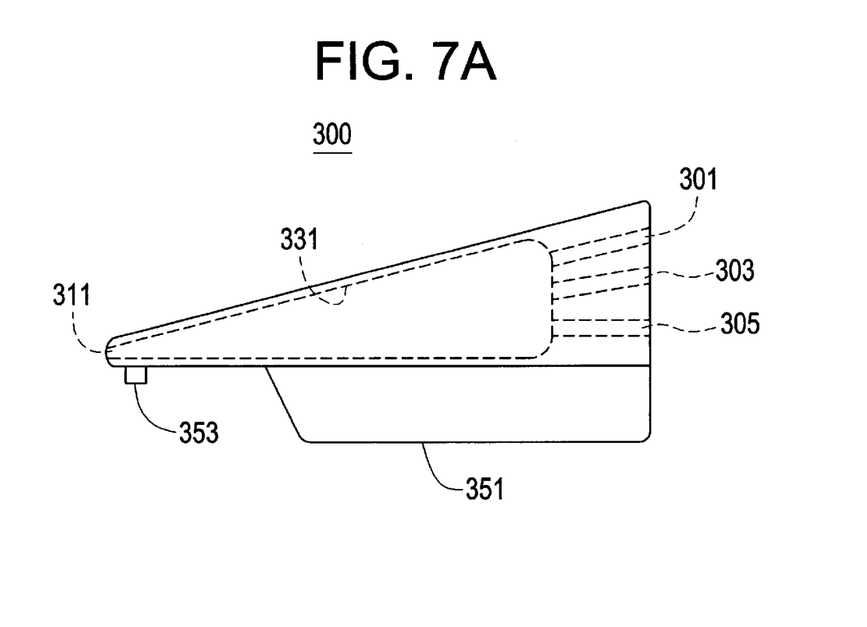
FIGS. 7A and 7B show the structure of a puncturing needle guide.
Figure 7B:
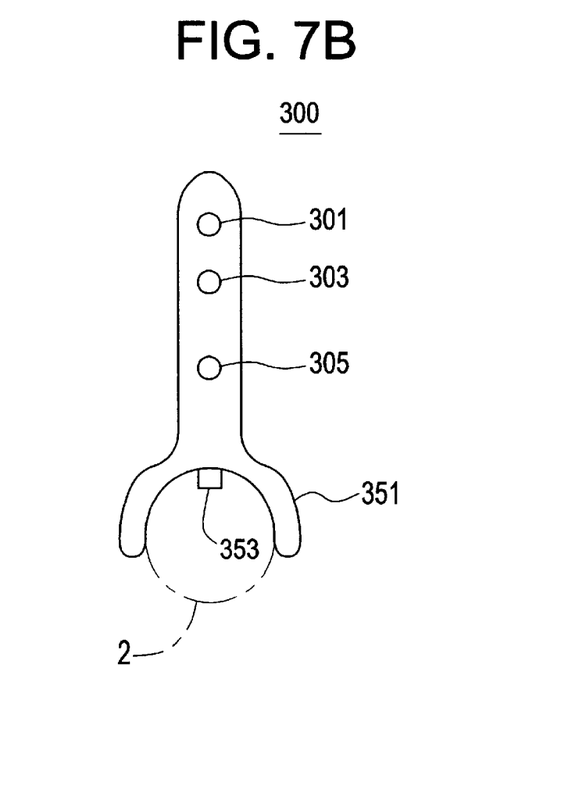

FIG. 7 schematically shows the structure of the puncturing needle guide 300. FIG. 7(a) is a side view, and FIG. 7(b) is a back view. As illustrated, the puncturing needle guide 300 is substantially a plate-like body. The width of the plate-like body diminishes gradually from one end thereof to the other end thereof. The overall length of the plate-like body is, for example, 150 mm. The width of the plate-like body at one end thereof is, for example, 20 mm, while the width thereof at the other end thereof is, for example, 3 mm.

A plurality of holes 301, 303, and 305 are formed in the end surface of the plate-like body at the end at which the width of the plate-like body is large. The number of holes is shown in FIG. 7 to be three. However, the number of holes is not limited to three but may be any value. The holes 301, 303, and 305 are arranged in a row in a width direction of the plate-like body. Hereinafter, the end of the plate-like body at which the width of the plate-like body is large may be called one end.

The holes 301, 303, and 305 are holes through which a puncturing needle can be passed. The holes 301, 303, and 305 are formed with metallic pipes or the like that are embedded in the plate-like body. A metal to be made into the metallic pipes is, for example, a stainless steel. Since the metallic pipes are adopted, the internal surfaces of the holes 301, 303, and 305 are hardly damaged.

A single hole 311 is formed in the end surface of the plate-like body at the end at which the width thereof is small. The hole 311 is a hole through which the puncturing needle can be passed. The hole 311 is opposed to the holes 301, 303, and 305 respectively. The end at which the width of the plate-like body is small may be called the other end.

A space interposed between the metallic pipes forming the holes 301, 303, and 305 and the hole 311 is a hollow 331. The holes 301, 303 and 305 and the hole 311 communicate with one another by way of the hollow 331. The internal surfaces of the hole 311 and hollow 331 are formed as metallic surfaces. A metal to be made into the metallic surfaces is, for example, a stainless steel. Since the metallic surfaces are adopted, the internal surfaces of the hole 311 and hollow 331 are hardly damaged.

The center of the hole 301 and the center of the hole 311 are linked by one straight line. The centers of the holes 303 and hole 311 are linked by another straight line. The centers of the holes 305 and 311 are linked by still another straight line. These three straight lines determine the direction of penetration in which the puncturing needle is penetrated. The puncturing needle guide 300 enables penetration in three different directions. The three directions are, for example, directions of 6°, 3°, and 0°. Herein, the direction parallel to the center axis of the ultrasonic probe 2 shall be the direction of 0°. Since the holes 301, 303, and 305 are linearly arranged in the end surface of the plate-like body, it is easy to grasp the directions of penetration.

The puncturing needle guide 300 has an attachment 351, by which the puncturing needle guide 300 is attached to the ultrasonic probe 2, formed on an edge thereof in a width direction thereof. The attachment 351 is structured to hug the ultrasonic probe 2. When the attachment 351 hugs the ultrasonic probe 2, the ultrasonic probe 2 has both sides thereof clamped with elastic force. Thus, the puncturing needle guide 300 is attached to the ultrasonic probe reliably. The lower edge of the attachment 351 extends beyond the portion of the ultrasonic probe 2 having the largest diameter.

The puncturing needle guide 300 has a projection 353 projecting to the lower surface thereof on the side thereof on which the hole 311 is formed. The projection 353 is fitted into a recess formed in the back of the ultrasonic probe 2 near the distal end thereof. The recess is a bottomed hole or groove. Consequently, the position in the ultrasonic probe at which the puncturing needle guide 300 is attached is determined.

With the puncturing needle guide 300 attached to the ultrasonic probe 2, the other end of the puncturing needle guide 300, that is, the end thereof at which the width thereof is small, and the ultrasound transmitting/receiving member 213 incorporated in the ultrasonic probe 2 are located on the same side of the ultrasonic probe 2. Consequently, as shown in FIG. 1, the ultrasonic probe 2 can be inserted into a body cavity of the object 4 together with the puncturing needle guide 300. In this state, any of the plurality of directions can be selected and a puncturing needle can be penetrated in the selected direction.

Figure 8:
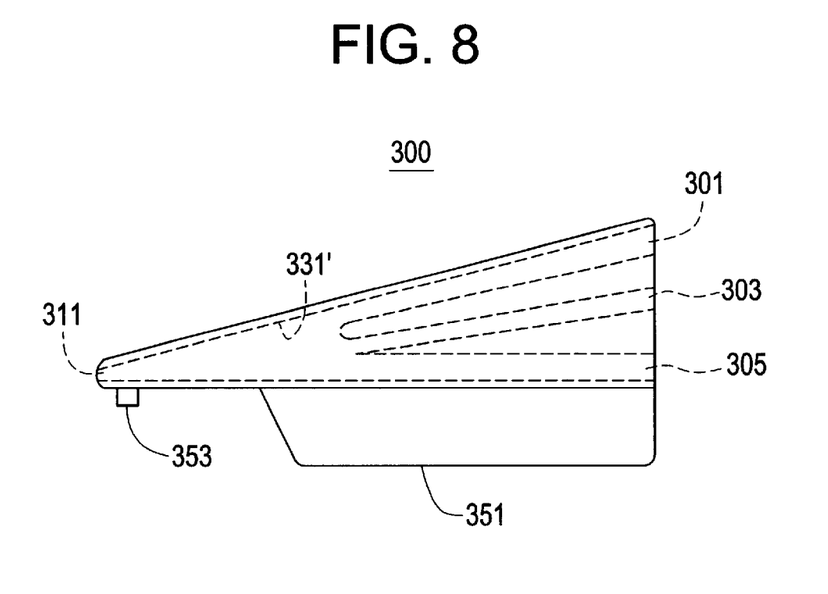
FIG. 8 shows the structure of a puncturing needle guide.

FIG. 8 shows another structure of a hollow allowing the holes 301, 303, and 305 and the hole 311 to communicate with one another. As illustrated, a hollow 331' is composed of three metallic pipes radiated from the hole 311 towards the holes 301, 303, and 305. The axial directions of the metallic pipes determine the directions of penetration.

The present invention has been described by presenting the examples of the preferred embodiments. Any person with ordinary skill in the art to which the present invention belongs can make various modifications or replacements without departing from the technical scope of the present invention. Consequently, the technical scope of the present invention encompasses not only the aforesaid embodiment but also all embodiments belonging to claims.

Many widely different embodiments of the invention may be configured without departing from the spirit and the scope of the present invention. It should be understood that the present invention is not limited to the specific embodiments described in the specification, except as defined in the appended claims.

What is claimed is:

1. A puncturing needle guide comprising:
    a plate-like body whose width diminishes gradually from one end thereof to the other end thereof;
    a plurality of holes which are formed in an end surface of the plate-like body at one end thereof and through which a puncturing needle can be passed, each said hole bounded by an internal surface of said plate-like body such that the internal surface circumscribes said hole;
    a single hole which is formed in an end surface of said plate-like body at the other end thereof and through which the puncturing needle can be passed, said single hole bounded by an internal surface of said plate-like body such that the internal surface circumscribes said single hole;
    a hollow that is formed as an internal space of said plate-like body and that allows said plurality of holes and said single hole to communicate with one another; and
    an attachment that is formed along one edge of said plate-like body in a width direction thereof and attaches said plate-like body to a rod-like ultrasonic probe such that said rod-like probe and said plate-like body can be at least partially inserted within a cavity of a patient.

2. The puncturing needle guide of claim 1, wherein said plurality of holes is arranged in a row in the end surface.

3. The puncturing needle guide of claim 1, wherein the internal surfaces of said plurality of holes are metallic surfaces.

4. The puncturing needle guide of claim 1, wherein the internal surface of said single hole is a metallic surface.

5. The puncturing needle guide of claim 1, wherein the internal surface of said hollow is a metallic surface.

6. The puncturing needle guide of claim 1, wherein said attachment enables attachment of said plate-like body to said rod-like ultrasonic probe, which has an ultrasound transmitting/receiving member incorporated in the distal part thereof, so that the other end of said plate-like body and the ultrasound transmitting/receiving member in said ultrasonic probe will be located on the same side of said ultrasonic probe.

7. An ultrasonic probe comprising:
a rod-like body having an ultrasound transmitting/receiving member incorporated in the distal part thereof
a plate-like body whose width diminishes gradually from one end thereof to the other end thereof
a coupler that is formed along an edge of said plate-like body in a width direction thereof and that couples said plate-like body to said rod-like body so that the other end of said plate-like body and the ultrasound transmitting/receiving member in said rod-like body will be located on the same side of said ultrasonic probe such that said rod-like body and said plate-like body can be at least partially inserted within a cavity of a patient;
a plurality of holes which are formed in an end surface of said plate-like body at one end thereof and through which a puncturing needle can be passed, each said hole bounded by an internal surface of said plate-like body such that the internal surface circumscribes the hole;
a single hole which is formed in an end surface of said plate-like body at the other end thereof and through which the puncturing needle can be passed, said single hole bounded by an internal surface of said plate-like body such that the internal surface circumscribes the single hole; and
a hollow that is formed as an internal space of said plate-like body and that allows said plurality of holes and said single hole to communicate with one another.

8. The ultrasonic probe of claim 7, wherein said plurality of holes is arranged in a row in said end surface.

9. The ultrasonic probe of claim 7, wherein the internal surfaces of said plurality of holes are metallic surfaces.

10. The ultrasonic probe of claim 7, wherein the internal surface of said single hole is a metallic surface.

11. The ultrasonic probe of claim 7, wherein the internal 'surface of said hollow is a metallic surface.

12. An ultrasound imaging apparatus comprising:
an ultrasonic probe for transmitting ultrasonic waves to an object and receiving echoes of the ultrasonic waves; and
an image producing means for producing an image on the basis of the received echoes, wherein:
said ultrasonic probe comprises:
a rod-like body having an ultrasound transmitting/receiving member incorporated in the distal part thereof;
a plate-like body whose width diminishes gradually from an end thereof to the other end thereof;
a coupler that is formed along an edge of said plate-like 'body in a width direction thereof and that couples said plate-like body to said rod-like body so that the other end of said plate-like body and the ultrasound transmitting/receiving member in said rod-like body will be located on the same side of said ultrasonic probe such that said rod-like body and said plate-like body can be at least partially inserted within a cavity of a patient;
a plurality of holes which are formed in an end surface of said plate-like body at one end thereof and through which a puncturing needle can be passed, each said hole bounded by an internal surface of said plate-like body such that the internal surface circumscribes said hole;
a single hole which is formed in an end surface of said plate-like body at the other end thereof and through which the puncturing needle can be passed, said single hole bounded by an internal surface of said plate-like body such that the internal surface circumscribes said single hole; and
a hollow that is formed as an internal space of said plate-like body and that allows said plurality of holes and said single hole to communicate with one another.

13. The ultrasound imaging apparatus of claim 12, wherein said plurality of holes is arranged in a row in said end surface.

14. The ultrasound imaging apparatus of claim 12, wherein the internal surfaces of said plurality of holes are metallic surfaces.

15. The ultrasound imaging apparatus of claim 12, wherein the internal surface of said single hole is a metallic surface.

16. The ultrasound imaging apparatus of claim 12, wherein the internal surface of said hollow is a metallic surface.

* * * * *